United States Patent [19]
De Brabander et al.

[11] Patent Number: 4,752,567
[45] Date of Patent: Jun. 21, 1988

[54] METHOD OF VISUALIZING INDIVIDUAL SUBMICROSCOPIC METAL PARTICLES

[75] Inventors: Marc J. De Brabander, Zoersel; Gustaaf M. A. Geuens, Mol; Rony M. Nuydens, Vosselaar; Marc K. J. J. Moeremans, Mol, all of Belgium

[73] Assignee: Janssen Pharmaceutica N.V., Beerse, Belgium

[21] Appl. No.: 622,923

[22] Filed: Jun. 21, 1984

[51] Int. Cl.$^4$ .................. G01N 33/53; H04N 5/14
[52] U.S. Cl. .................................. 435/7; 422/55; 422/61; 424/3; 435/29; 435/810; 436/503; 436/518; 436/525; 436/534; 436/539; 436/540; 436/805; 436/807; 358/166
[58] Field of Search .............. 436/503, 518, 525, 534, 436/539, 540, 805, 807; 435/7, 810, 29; 422/55, 61; 424/3; 358/166

[56] References Cited
U.S. PATENT DOCUMENTS 4,313,734 2/1982 Leuvering .............. 436/503
4,420,558 12/1983 De May et al. ......... 436/519
4,446,238 5/1984 De May et al. ......... 436/527

OTHER PUBLICATIONS

Leuvering et al, J. Immunoassay, 1(1) 77-91 (1980).
Leuvering et al, J. Immunol. Methods, 45 (1981) 183-194.
Leuvering et al, J. Immunol. Methods, 60 (1983) 9-23.
Leuvering et al, J. Immunol. Methods, 62 (1983) 175-184.

Primary Examiner—Christine M. Nucker
Attorney, Agent, or Firm—Geoffrey G. Dellenbaugh

[57] ABSTRACT

A method of visualizing individual submicroscopic metal particles by subjecting said particles to bright field or epi-polarization microscopy and enhancing the contrast of the image so obtained by electronic means.

13 Claims, No Drawings

METHOD OF VISUALIZING INDIVIDUAL SUBMICROSCOPIC METAL PARTICLES

During the last years, small size metal particles, in particular colloïdal gold particles, have increasingly been used as markers for the locatization, characterization and quantitation of specific organic substances and structures. Usually, such organic substances and structures are of biological origin and their determination by means of metal labelling has proven useful in various areas of biochemistry, pharmacology, cytology and histology. The concerned techniques have found widespread use, not only in purely scientific research but also in practical applications for routine use, e.g. in diagnostic procedures.

In principle, the use of colloïdal metal particles as markers is based on the property of such particles to bind polymers, such as, nucleic acids, polysaccharides, and the like, and the property of these polymers to interact in a direct or indirect manner with specific organic substances and structures. In general such interactions will be based on acceptor-ligand complex formations, such as antigen-antibody, receptor-ligand, and the like interactions and hence, immunological determinations are the preferred field of application of techniques based on colloïdal metal marking, whereby gold sols are predominantly used as metal particles.

In J. Histochem. Cytochem., 25, 1187 (1977) there is described a method of coating colloïdal gold with particular proteins and a method of using gold particles coated with specific proteins as markers for the detection of specific cell-surface antigens by means of electron microscopy.

In U.S. Pat. No. 4,313,734, there is broadly described a method for the detection and/or determination of one or more components of the reaction between a specific binding protein and the corresponding bindable substance, thereby using one or more components coupled to appropriate metal particles. The detection and/or determination of the reaction product or complex so formed is done indirectly, making use of the physical properties of the metal contained in the relevant fractions. According to the reference, the determination can be done following known methodologies, such as, for example, visual inspection or colorimetry of the metal in dispersed form, flame emission spectrophotometry and frame-less atomic absorption spectrophotometry. In essence, the method is concerned with interactions of the immunological type and is this form it is generally referred to as the Sol Particle Immuno-Assay (SPIA).

Recently, there have been described improved and simplified methods for the visualization of immobilized metal-labelled complexes or metal-labelled structures, whereby bright field microscopy is used as a primary detection means. For example, in U.S. Pat. No. 4,420,558 there is described a bright field light microscopic method for enumerating and characterizing subtypes of blood cells and their precursors, which comprises the labelling of said cells and precursors with gold-labelled antibodies under well-defined circumstances. As set out in the reference, the visualization of labelled cell surfaces is based on the aggregate properties of the gold particles, which, under the indicated circumstances, undergo extensive patching.

U.S. Pat. No. 4,446,238 describes the use of colloïdal gold as a bright field light microscopic marker for the immunocytochemical localization of defined antigens in histological sections. Again the microscopic detection is based on the observation of the intense reddish colour, resulting from the accumulation of large numbers of gold granules over antigen-containing surfaces.

Typically, in the above-mentioned procedures, the employed metal particles have a diameter of from about 10 to about 100 nm. This is well below the resolution limit of bright field light microscopy, which is generally accepted to lie around 200 nm. It is therefore quite logical that all previously known visual light microscopic methods are limited in their applications to the detection of immobilized aggregates of metal particles. Individual particles could be observed with ultramicroscopic techniques only, in particular with electron microscopy.

It has now quite surprisingly been found that individual metal particles of a diameter smaller than 200 nm can be made clearly visible by means of bright field light microscopy or epi-polarization microscopy in the visible spectrum, provided that the resulting image is subjected to electronic contrast enhancement. In spite of the completely unexpected and most surprising possibilities offered by the present invention, it should be observed that it is not in conflict with any established law of nature. The limit of resolution is usually defined as the closest distance between two small objects that can be distinguished as being separate. For light microscopy in the visible spectrum, this limit is accepted to be about 200 nm. In general, this is at the same time the minimal section of a particle or structure that can be observed by visual light microscopy. The fact that we have now made it possible to visualize and optionally characterize single metal particles of a diameter smaller than 200 nm, and even smaller than 20 nm, therefore constitutes a significant progress of the art.

Albeit true that the combination of light microscopy with electronic contrast enhancement by means of a video camera has been reported to enable the visualization of certain structures with dimensions smaller than 200 nm, none of the described achievements can be compared with the present realization in terms of detection limit and optical clarity. In Cell Motility, 1, 275–289 (1981) it is taught that microtubules, having a diameter of about 25 nm can be visualized by means of Video-Enhanced Contrast, Differential Interference Contrast (AVEC-DIC) Microscopy. It should be observed however, that microtubules are linear structures, the length of which largely surpasses 200 nm. Moreover, it is easier to observe small particles or structures in movement than when they are at rest. In contrast herewith, the subject invention is concerned with visualization of single, essentially spherical, particles of submicroscopic dimensions which may be at rest or in movement.

In TINS, April 1984, 112, it is further said that the AVEC-DIC techniques has been used to detect the movement of intra-axonal organelles that are below the conventional limit of resolution, and, that a faint stream of what are apparently very small vesicles (perhaps 30–50 nm) was observed. Again the disclosure in this reference is restricted to the observation of particles in movement, which become visual as a faint stream only. Quite differently, the process of the subject invention allows the visualization of both moving and resting submicroscopic metal particles with such clarity and contrast that the particles can be easily distinguished from the non-metallic-surroundings and that their detection and optional counting can even be automated.

In view of its simplicity and reliability, the process according to the invention substantially simplifies the detection of submicroscopic metal particles and opens new perspectives for the use of such particles as diagnostic tools. In principle, the process can be used for the localization, determination and/or characterization of metal particles of a diameter smaller than 200 nm in any non-metallic surrounding which lends itself to light microscopic inspection. For example, it can be employed to visualize metal particles of any nature, having a diameter of from about 1 to 200 nm, preferably from 5 to 200 nm in any essentially transparent substrate, or at the surface of transparent or non-transparent substrates. Obviously, determination at the surface of non-transparent substrates will require epi-luminescence, in particular epi-polarization microscopy. The determination may be solely qualitative or quantitative. In the latter case, quantitative measurement can be carried out simply by counting the number of particles in a field of predetermined size. As examples of metals, of which particles of the indicated size can be visualized according to the claimed method, there may be mentioned gold, silver, platinum, copper, as well as iron, nickel, zinc, chromium, titanium, manganese, cobalt, molybdenum, rhodium, palladium, cadmium, osmium, iridium, mercury, aluminum, etc. Preferred applications will be found in the detection and determination of nobel metal particles, in particular of gold, silver and platinum.

The purpose of such determinations may either be the localization and/or quantitation of such particles themselves, or, the localization and/or identification and/or quantitation of specific substances or structures which bind themselves directly or indirectly to such particles. In its first aspect, the invention provides a handsome and reliable method of determining metal particles in any suitable liquid, semi-solid or solid medium, e.g. in metal sols suspended in an aqueous or organic medium. Moreover, the ease with which the method is carried out makes it attractive to use metal particles of the indicated size as tracers to investigate the homogeneity of binary or multicomponent systems upon mixing, or, to study the flow characteristics of liquid, semi-solid or solid, in particular amorphous media, or to determine the thickness of liquid or solid film coatings, etc.

In its second aspect, the method may find application in the determination of specific organic substances or structures, mostly of biological origin, both in vitro and in vivo. Such applications, which in general will make use of metal sol particles, in particular gold particles, coupled to well-defined organic substances, will in principle comprise but not be limited to instances where at present gold-labelling is known to be useful. As such, the claimed method will afford considerable progress and convenience of operation in such domains as cytology, histology, intra- and extracellular diagnosis of biological substances etc. One of the major advantages of the subject method is that, at least in principle, it is non-destructive and can be applied on intact structurally organized—in particular biological—systems. For example, by using metal particles coupled to specific proteins, e.g. antibodies, and allowing those to interact with suitable bindable substances, the exact localization of the latter can be carried out with ease and in an essentially non-destructive manner. The fact that very small particles can be used makes it possible to observe the above-described phenomena in a micro-environment, e.g. in one—if desired living—cell. Hence, the subject method may be employed to localize and/or quantitate specific bindable substances and/or structures in individual cells, and/or to follow their distribution and/or movements within a cell, and/or to determine the velocity of certain transport phenomena within the cell. Examples of specific intracellular transport phenomena, which can be easily observed with the subject method, even in living organisms, include microtubular and axonal transport. The determination of axonal transport in living nerve biopsies may, for example, be used as a diagnostic tool to investigate conditions like muscular distrophy or to follow the evolution of such diseases. The method may further be used to detect various kinds of viral infections.

Due to its general character, the method may be used in diagnostic tests based on the detection of surface antigens or intracellular antigens or, in general, of any specific organic substances in biological media or derived fractions. Usually, such substances will have a polypeptide nature, such as, for example, hormones, proteins, enzymes etc. In principle, it will be possible to apply a diagnostic technique, based on the present method on a single cell. In view of its non-destructive character, the method can therefore be used advantageously to distinguish single cells with deviating biochemical properties from other cells, whereby the selected cell remain perfectly viable and can be further cultivated. Such applications will be particularly useful in procedures of genetic manipulation, namely to quickly separate positive from negative expressor cells. It is also suitable for the detection of genetic deviation or metabolic deficiencies in prenatal organisms.

Compared with existing diagnostic methods based on sol particle immuno assays, the present method has a much greater sensitivity. Indeed, existing methods are in general based on light absorption or scattering by the bulk of absorbed or suspended metal particles. Obviously, the observation of colour, e.g. on a blotting medium, requires the presence of massive numbers of particles. In contrast therewith, the present method makes it possible to observe and count single particles. Hence, the present method will largely facilitate the development of diagnostic blots for applications where existing, e.g. visual or colorimetric, techniques are too less sensitive, e.g. for the detection of Hepatitis.

In the field of pharmacology, the method will be a valuable aid to follow the cellular and subcellular localization of pharmaca and their receptors.

The preparation of sol particles, in particular gold particles, their coupling to suitable binding substances, e.g. antibodies, and the various methodologies of combining them, directly or indirectly, with the desired bindable substances are sufficiently known. In this connection, reference may be made e.g. to Immunohistochemistry, Cuello, A. C. (ed.), IBRO handbook series, Wiley, Ney York, 1983, p. 347-372; U.S. Pat. No. 4,313,784 and Immunocytochemistry, Polak, J. M. and Van Noorden, S. (ed.), Wright PSG, Bristol, 1983, p. 82-112.

The method of visualizing metal particles according to the present invention can be carried out using currently available equipment. Such equipment will comprise an appropriate light microscope on the one hand, and, on the other hand, an electronic contrast enhancement device. As an appropriate light microscope, there may be used any standard good quality microscope, equipped for bright field and/or epi-polarization microscope. The use of monochromatic light is not essential but improves the quality. In practice, monochromatic green light has proven to give excellent results. When bright field microscopy is employed, a further improvement can be reached by using the differential interference contrast (DIC) technique. As an electronic contrast enhancement device, and of the usual types of video cameras, equipped with manual or automatic brightness and contrast control will be suitable. Of course, the quality of the images will be directly related to the precision of the instrument.

When using the method according to the invention, and in order to distinguish the concerned metal particles to the greatest possible extent from the surrounding substrate, it will be appropriate to use a greater working aperture than required for optimal visualization of the substrate. In practice, the best results are obtained when working at full or nearly full aperture, i.e. under circumstances where the direct microscopic image has, due to its excessive brightness, almost no contrast and is for that reason completely inadequate for visual examination. When properly viewed and processed with a video camera, whereby most of the stray light will be cut-off and the contrast enhanced, the metal particles will become clearly visible as well-defined discrete spots. Under bright field microscopy, the spots will be dark against a bright background, while under epi-polarization microscopy, the particles will become visible as bright sparkling spots. If the microscope allows transition from bright field to epi-polarization microscopy, without field re-adjustment, the alternate visualization of the particles by both techniques gives an excellent confirmation of their identity.

In view of the clarity with which the metal particles are visible on the processed image, their detection and quantitation in an appropriate substrate can be easily automated, using any usual type of automatic counting equipment.

The invention is further illustrated by the following example which is by no means intended to limit the scope thereof.

EXAMPLE

PROBING MICROTUBULE-DEPENDENT INTRACELLULAR MOTILITY WITH NANOMETER PARTICLE VIDEO ULTRAMICROSCOPY (NANOVID ULTRAMICROSCOPY)

Method: Nanoparticle video ultramicroscopy or Nanovid ultramicroscopy

PTK (Potorous Tridactylis Kidney) cells were used 24–48 h after seeding on glass coverslips. Collodial gold particles, having a size of 20–40 nm and coated with serum albumin (Nordic), were stabilized with polyethyleneglycol. The size distribution was determined ultrastructurally. Micro-infection was done on an inverted contrast microscope. Glass capillaries drawn to a tip opening of ±1 µm were back-filled by capillary action. Immediately after injection the coverslip was removed from the Petri dish and mounted on a slide using Parafilm strips as spacers and Valap (vaseline, lanoline, parafine ⅓ of each) to seal the microchamber. The preparation was then mounted on a Reichert (Wien, Austria) Polyvar microscope. The temperature of the preparation was kept at 37°±1° C. by an airstream incubator. The microscope was equipped with a universal condenser and a 100×planapo lens. Köhler illumination was achieved throughout the observation period using oil immersion of both the condenser and objective lens. By switching condenser settings or filter units the same cells can be observed within less than 30 sec with the following optical set-ups in sequence: transmitted light, differential interference contrast (DIC), interference reflection microscopy using a dichroic mirror and crossed polarizer and analyzer, epifluorescence, dark field observation or phase contrast using a 100×planapo phase contrast objective lens. With transmitted light or DIC the full numerical aperture of the system was used. Illumination was by the green line of a 100 Watt halogen lamp or of a 200 Watt mercury arch. The image (approximately the central 20% of the whole field) was projected directly onto the face plate of a Panasonic WV-1800 video camera providing a horizontal resolution of 800 TV lines. The video signal was fed into a Panasonic WV 5340 monitor and a Sony VD-5850P U-matic videocassette recorder providing a horizontal resolution of 340 lines. Recordings were made in real time or in the time lapse mode using an AC 580 animation control unit build by EOS for the Sony recorder. As a rule the recorder was instructed to grab 2 frames every 10 seconds. Playback at normal speed (25 frames/sec) was thus at an acceleration of 125 times. Photographic recordings were made from the monitor using real time playback or still pictures when the recording was done in the time lapse mode. Shutter time was between ¼–⅛ sec.

Quite unexpectedly when the condenser was turned to normal bright field transmission and the illumination was increased to completely saturate the camera, clearly defined dark spots appeared on the screen on an entirely white background. The gold particles reflected polarized light and produced enough dichroic effects because the light passed through the crossed analyzer. They appeared as brightly shining dots on a background consisting of the usual interference reflection picture of the cell. Except for very large aggregates, usually located in the cell centre, no dots were visible through the oculars and none could be recorded on the photographic plate. Using Normanski differential interference contrast (DIC) even the smallest particles were easily detected. However, they can not be discerned from endogenous organelles unless there is switched back and forth to bright field observation. In order to detect individual gold particles cells grown on formvar-coated grids with 20 or 40 nm gold were injected and recorded on video tape and fixed immediately afterwards by perfusion with glutaraldehyde. They were then further processed for whole mount electron microscopic observation. Similar experiments were done with naked grids onto which the gold sol was adsorbed. Both exercises clearly demonstrated that most of the smallest dots were individual gold particles. Small aggregates of 2–3 particles appeared as having the same size. Larger aggregates, of which there were few, were probably produced in the capillary tip of the micropipette, which became often clogged when using the 40 nm size. They appeared on the screen as globules of 0.5–1 µm. Whole mount electron microscopy, in particular using stereo photographs was also helpful in showing that most gold particles were free in the cytoplasm, often closely associated with microtubules. Vital staining of the cells with acridine orange to demonstrate the lysosomal compartment showed no gold particles within these organelles, although this was clearly the case when cells were fed the same particles in the medium. Rather frequently gold particles were seemingly attached to a small vesicle which itself was connected to a microtubule.

Videotape analysis showed that, although microinjection was always done close to the nucleus, the gold particles were dispersed throughout the cells, within 10–15 min. Observation in real time and in the time lapse mode showed that all particles moved along linear tracks towards and away from the centrosome in a typical saltatory fashion. In particular the individual particles (both 20 and 40 nm) were altervatively engaged in typical linear movement and local irregular "jumping around". The latter type of movement was, however, much slower than true Brownian motion of gold particles in the medium. While the small particles remained dispersed in the cytoplasm up to 2–4 h after injection, the larger ones tended to accumulate in the centrosomal area. Analysis of speed and frequency of saltation for different sizes of gold aggregates and comparison with endogenous organelles disclosed a virtual identity in their behavior which interestingly depended on the respective size. The effects of the microtubule inhibitor nocodazole ($10^{-6}$–$10^{-5}$ M) were quite predictable and identical for both endogenous organelles and gold particles. Saltation disappeared gradually, only irregular local movement persisted. Sodium azide ($10^{-2}$ M) arrested saltation within a few minutes corresponding to a rapid depletion of ATP. The effects of taxol were intriguing. Small particles continued saltation, often along peripheral microtubule bundles. Larger aggregates, however, were completely arrested. Interestingly, acridine orange, a protein cross linker, not only arrested saltation but also the local irregular movements unlike any of the other drugs.

Microtubules are clearly involved in saltatory motion. Because treadmilling of subunits has been suggested to be a possible molecular mechanism, 40 nm particles coupled to a monoclonal anitbody to tubulin were injected. It was first confirmed that microinjected fluorescently-labelled antibody covers the entire microtubule system in the cells but has no effects on saltation, cell shape and movement or mitosis at concentrations below 6 mg/ml (injection solution). In some cells most of the gold particles assumed an entirely fixed immotile position within 10–15 min and stayed immotile for more than 2 h. Few particles detached and reattached at another place during the observation period. Often the particles formed clearly linear arrays converging towards the centrosome. Switching to DIC showed normal movement of endogenous organelles often along tracks delineated by the gold particles. In other cells a variable number of particles was not fixed but saltated. It is assumed that these had no free tubulin binding site, either by absence of antibody or by masking of the antigen binding site, e.g. by free tubulin subunits. The amount of free subunits may very well depend on the cell cycle stage.

In cells injected during prophase some particles saltated along the aster microtubules. Many were also seen within the spindle which was devoid of detectable endogenous organelles. Most interestingly they jumped up and down not only along spindle fibers but also laterally through the spindle. Few particles assumed a stationary position. One was seen attached to a kinetochore fiber close to a centromere, at metaphase. It moved along with it through anaphase. When it became entrapped within the telophase nucleus it was detached from the chromatin. At that time the gold particle started to move in a very fast typical Brownian motion within a pocket between the chromatids. Particles in the medium jump at the same speed. Then its movement suddenly slowed down to the same level as that seen in the cytoplasm of, e.g. nocodazole-treated cells.

What is claimed is:

1. A method of visualizing individual metal particles of a diameter smaller than 200 nanometer, which comprises subjecting said particles to bright field or epipolarization microscopy and enhancing the contrast of the image so obtained by means of a video camera.

2. A method of visualizing individual metal particles of a diameter smaller than 200 nanometer, which comprises subjecting said particles to bright field or epipolarization microscopy using a working aperture substantially greater than optimal for direct visual inspection of the microscopic image and enhancing the contrast of the image so obtained by means of a video camera.

3. A method according to claim 1 wherein the said metal particles are gold particles.

4. A method of detecting and/or determining specific organic substances bindable to specific binding proteins, which comprises the steps of (i) labelling the reaction product of said bindable substance with the said binding protein using metal particles of a diameter between 1 and 200 nanometer and (ii) visualizing individual metal particles of the so labelled reaction product by a method as claimed in any one of claims 1 and 2.

5. A method according to claim 4 wherein the labelling of said reaction product is carried out by reacting the said bindable substance with a binding protein which is coupled directly to the said metal particles.

6. A method according to claim 4 wherein the said bindable substance and the said binding protein undergo a ligand-receptor interaction.

7. A method according to claim 4 wherien the said bindable substance and the said binding protein undergo an immunological reaction.

8. A method according to claim 7 wherein the said bindable substance is an antigen and the said binding protein is an antibody to said antigen.

9. A method according to claim 7 wherein the said antigen is selected from the group consisting of a cell surface antigen, a hormone, an enzyme and an intracellar element.

10. A method according to claim 8 wherein said antibody is coupled directly to the said metal particles.

11. A method according to claim 8 wherein the reaction product of said antigen and said antibody is further reacted with a second bindable substance which is coupled to the said metal particles.

12. A method according to claim 4 wherein the metal particles have a diameter between 1 and 40 nm.

13. A method according to claim 4 wherein the metal particles have a diameter between 1 and 20 nm.

* * * * *